United States Patent [19]
Tsuji et al.

[11] Patent Number: 5,881,596
[45] Date of Patent: Mar. 16, 1999

[54] URINE SAMPLING VESSEL

[75] Inventors: Akira Tsuji; Ichiro Morimoto, both of Osaka; Takahiro Matsumoto, Tokyo, all of Japan

[73] Assignee: Itochu Corporation, Osaka, Japan

[21] Appl. No.: 817,617

[22] PCT Filed: Sep. 28, 1994

[86] PCT No.: PCT/JP94/01587

§ 371 Date: Mar. 28, 1997

§ 102(e) Date: Mar. 28, 1997

[87] PCT Pub. No.: WO95/09362

PCT Pub. Date: Apr. 6, 1995

[30] Foreign Application Priority Data

Sep. 30, 1993 [JP] Japan ..................................... 5-245423
Jun. 22, 1994 [JP] Japan ..................................... 6-140548

[51] Int. Cl.[6] ............................................... G01F 19/00
[52] U.S. Cl. ............................. 73/426; 600/574; 422/102
[58] Field of Search ................ 73/426, 864; 600/573, 600/574; 422/102; 215/DIG. 3; 206/499, 515

[56] References Cited

U.S. PATENT DOCUMENTS

| | | | |
|---|---|---|---|
| 2,587,221 | 2/1952 | Richardson et al. | 422/102 X |
| 3,579,303 | 5/1971 | Pickering | 422/102 X |
| 3,607,098 | 9/1971 | Strande | 422/102 |
| 3,807,955 | 4/1974 | Note, Jr. et al. | 422/102 X |
| 4,094,641 | 6/1978 | Friswell | 422/102 X |
| 4,576,185 | 3/1986 | Proud et al. | 600/574 |
| 4,873,193 | 10/1989 | Jensen et al. | 422/102 X |
| 4,948,000 | 8/1990 | Grabenkort | 215/12.2 |
| 5,246,434 | 9/1993 | Ebara | 600/574 |
| 5,288,466 | 2/1994 | Burns | 422/102 |
| 5,334,348 | 8/1994 | Saito et al. | |
| 5,384,096 | 1/1995 | Burns | 422/102 |
| 5,458,854 | 10/1995 | Burns | 422/102 |

FOREIGN PATENT DOCUMENTS

| | | | |
|---|---|---|---|
| 58-66053 | 4/1983 | Japan | 73/426 |
| 1-102364 | 4/1989 | Japan . | |
| 6-27103 | 2/1994 | Japan . | |
| 6-148176 | 5/1994 | Japan . | |
| 6-281647 | 10/1994 | Japan . | |
| 3490 | 11/1904 | United Kingdom | 73/426 |
| 2015158 | 9/1979 | United Kingdom | 422/102 |

*Primary Examiner*—George Dombroske
*Assistant Examiner*—Paul D. Amrozowicz
*Attorney, Agent, or Firm*—Sixbey, Friedman, Leedom & Ferguson; David S. Safran

[57] ABSTRACT

A cylindrical vessel body 20 has an end opened. A urine taking cap 50 comprises a fitting cylinder section 51 which can be freely fitted in tight contact with the opened end of the vessel body 20, a urine sampling cylinder section 52 connected to the fitting cylinder section 51 and having a urine sampling inlet 5b opened thereon, and a grip section 53 connected to an outer end of the urine sampling cylinder section 52. In addition, a cover cylinder 30 has an end opened, the opened end being capable of being fitted in tight contact with a tapered face 5e of the urine sampling cylinder section 52 in the state in which the vessel body 20 having the urine taking cap 50 attached thereto is inserted. A ring protrusion 55 is formed on an outer peripheral face of a connecting portion of the urine sampling cylinder section 52 and the grip section 53, and the grip section 53 can be freely extended axially by an extension cylinder 5g.

17 Claims, 23 Drawing Sheets

URINE SAMPLING VESSEL

[TECHNICAL FIELD]

The present invention relates to a urine sampling vessel to be used for a urinalysis executed in hospitals, examination centers and the like.

[BACKGROUND ART]

In general, while a urinalysis is a simple examination with which an examinee does not feel pain and an examiner does not make a lot of burden, it can give important information related to the examinee's state of health to foretell internal disorders and the like.

In recent years, therefore, various urinalyses are executed for new patients, people who get a physical checkup, inpatients and the like in the hospitals and the examination centers.

In this urinalysis, conventionally, the examinee takes urine in a cup and puts the cup having the urine on a housing shelf provided in a lavatory. These cups are moved from each lavatory to an examination room. After the cups are collected to some extent, the urinalysis is performed.

-Problems to be Solved-

However, a method for taking urine in a cup and examining the urine described above has had the following problems.

(1) In particular, it is hard for most women and old people to accurately take the urine in the cup. There is a possibility that the urine might not get in the cup but spill to make hands, clothes and the like dirty. For this reason, it is unsanitary.

(2) Under the circumstances that various urinalyses are performed, a lot of cups are arranged vertically and horizontally. For this reason, a considerable space is required to keep the cups until the examination is performed.

(3) There is a possibility that the cups might be dropped or tilted to spill the urine when moving and carrying the cups from the lavatory to an examination room. As a result, there is a fear that the examination cannot be performed or surroundings might be made dirty.

(4) In some cases, an amount of the taken urine considerably exceeds an amount necessary for the examination. For this reason, when many examinees' urine is collected, it smells strongly. Consequently, doctors and nurses perform the urinalyses with lower efficiency of work.

As means for solving the above-mentioned problems, a urine sampling vessel has been disclosed in Japanese Unexamined Patent Publication No. 6-27103. The urine sampling vessel comprises a slender vessel body having a plurality of urine sampling holes, and a cap connected to an end of the vessel body for inserting the vessel body to be freely slided. Urine is taken through the urine sampling holes with the vessel body pulled out of the cap. After taking the urine, the vessel body is inserted in the cap to seal the cap and the vessel body at the end so as to be carried to the examination room and the like.

In the above-mentioned urine sampling vessel, however, the cap also serves as a grip section when taking the urine. Consequently, when covering the vessel body with the cap after taking the urine, it is necessary to grip the vessel body to which the urine sticks. Therefore, there has been a problem that the work of sealing the vessel body is very unsanitary.

After taking the urine, a lower end of an opening of the cap tightly comes in contact with a skirt portion of a lower end of the vessel body. However, the urine sometimes leaks between the vessel body and the cap during carrying, and the cap is pulled out upward. Therefore, there has been a problem that hands might be made dirty by the leaking urine when the cap is removed with the vessel body gripped during an examination.

In many cases, the urinalysis is currently performed by using an examination apparatus. In the case where this examination apparatus is used, the vessel body cannot exactly be applied to the examination apparatus, that is, it cannot serve as a sample vessel of the examination apparatus because the vessel body has the urine sampling holes and the like in the urine sampling vessel. Consequently, there has been a problem that the taken urine should be emptied out of the vessel body into the sample vessel for the examination.

[DISCLOSURE OF THE INVENTION]

In consideration of the above-mentioned respects, it is an object of the present invention to provide a urine sampling vessel which can take urine sanitarily and easily and can also be used directly for an examination apparatus.

-Structure-

In order to attain the above-mentioned object, means according to the present invention is characterized in that a vessel body having a removable cap can be covered with a cover cylinder.

According to means of the invention as defined in claim 1, specifically, there is first provided a slender cylindrical vessel body having an end blocked and the other end opened, and having a urine sampling inlet opened in a central portion thereof.

Furthermore, there is provided a cover cylinder having an end blocked and the other end opened, formed such that the vessel body can be freely inserted in tight contact therewith and pulled out thereof, and put on the vessel body so as to block the urine sampling inlet.

In addition, there is provided a cap having a blocking plug section formed thereon, the blocking plug section being freely removed from and attached to the opened end of the vessel body so as to open and close the opened end of the vessel body.

According to means of the invention as defined in claim 2, in the invention as defined in claim 1, the blocking plug section of the cap is protruded from an end of a cap body, and is formed like a short column so as to be freely inserted in pressure contact with the opened end of the vessel body and pulled out thereof.

Furthermore, the cap body has a holding hole formed thereon, the holding hole being opened on the other end face of the cap body and causing the end of the cover cylinder to be freely inserted therein and removed therefrom.

According to means of the invention as defined in claim 3, in the invention as defined in claim 1, the vessel body has an examination opening for a urinalysis formed from the urine sampling inlet toward an opened end side.

According to means of the invention as defined in claim 4, in the invention as defined in claim 1, a cap body has an engagement groove formed thereon, the engagement groove being connected to an outer periphery of a base end of the blocking plug section and causing the opened ends of the vessel body and the cover cylinder to be inserted therein with the vessel body inserted in the cover cylinder.

According to means of the invention as defined in claim 5, in the invention as defined in claim 1, the vessel body has a protrusion formed on an outer peripheral face thereof, to which the cover cylinder is attached by pressure when putting on the cover cylinder.

According to means of the invention as defined in claim 6, in the invention as defined in claim 1, a flange section extending outward is formed on an end on a blocking plug section side of a cap body.

According to other means of the present invention, the urine taking cap having the urine sampling inlet is attached to the vessel body and the cover cylinder for covering the vessel body and a part of the urine taking cap is formed so as to be freely fitted in tight contact with the urine taking cap.

According to means of the invention as defined in claim 7, specifically, there is first provided a cylindrical vessel body having an end blocked and the other end opened, and capable of housing taken urine.

There is provided a urine taking cap having a hollow fitting cylinder section formed like a cylinder which can be freely fitted in tight contact with the opened end of the vessel body and having both end faces opened, a urine sampling cylinder section formed like a cylinder which is connected to an outer end of the fitting cylinder section and has an outer end side blocked and having a urine sampling inlet penetrating from an outer peripheral face to an inner peripheral face opened on an inner end side, and a grip section formed in connection to an outer end of the urine sampling cylinder section so as to be freely gripped.

In addition, there is provided a cover cylinder having an end blocked and the other end opened, and formed to cause the vessel body to be freely inserted therein and pulled out thereof, the opened end closing the urine sampling inlet of the urine taking cap and capable of being fitted in tight contact with the outer peripheral face of the outer end of the urine sampling cylinder section in the state in which the vessel body having the urine taking cap attached thereto is inserted.

According to means of the invention as defined in claim 8, in the invention as defined in claim 7, the outer peripheral face of the outer end of the urine sampling cylinder section in the urine taking cap has a tapered face formed thereon, whose diameter is increased toward an outer end such that the opened end of the cover cylinder is fitted in tight contact therewith.

According to means of the invention as defined in claim 9, in the invention as defined in claim 7, a ring protrusion is formed on an outer peripheral face of a connecting portion of the urine sampling cylinder section and the grip section.

According to means of the invention as defined in claim 10, in the invention as defined in claim 7, the grip section of the urine taking cap has a grip body in which an extension cylinder having a bottom or no bottom is fitted so as to be freely slided.

According to means of the invention as defined in claim 11, in the invention as defined in claim 7, the urine sampling inlet of the urine taking cap is formed by cutting out a half of the urine sampling cylinder section in a circumferential direction.

According to means of the invention as defined in claim 12, in the invention as defined in claim 7, the grip section of the urine taking cap has a holding hole opened on an outer end face thereof and capable of causing the end of the cover cylinder to be freely inserted therein and removed therefrom.

-Function-

With the above-mentioned structure, the cap is first attached to the opened end of the vessel body at the blocking plug section when taking the urine according to the invention as defined in claim 1, and the cover cylinder is inserted in the holding hole of the cap to bring into the urine taking state according to the invention as defined in claim 2.

In the assembled state, an examinee grips the cap with the blocking end side of the vessel body turned downward and passes urine over the urine sampling inlet. Consequently, the urine is injected from the urine sampling inlet into the vessel body so that the urine is taken into the vessel body.

When the work of taking the urine is terminated, the cover cylinder is pulled out of the cap with the blocking end side of the vessel body turned downward and the vessel body is inserted in the cover cylinder. By putting the cover cylinder on the vessel body, the urine sampling inlet is closed and the examination opening is also closed according to the invention as defined in claim 3.

According to the invention as defined in claim 4, the opened ends of the cover cylinder and the vessel body are inserted in the engagement groove of the cap so that both opened ends of the cover cylinder and the vessel body are blocked. According to the invention as defined in claim 5, the protrusion of the vessel body tightly comes in contact with the cover cylinder to obtain non-slip.

In the state in which the vessel body is inserted in the cover cylinder, they are inserted in a vessel holder or the like and carried to an examination room or the like.

Then, when performing the urinalysis, the cap is removed with the vessel body inserted in the cover cylinder and a reagent, a test paper or the like is inserted through the opened end of the vessel body, or the cover cylinder is slightly pulled out of the vessel body with the cap attached to the vessel body to open only the examination opening and the reagent, the test paper or the like is inserted through the examination opening to perform the examination.

According to the invention as defined in claim 7, the urine taking cap is first attached to the opened end of the vessel body at the fitting cylinder section to bring into the urine taking state when raking the urine. According to the invention as defined in claim 10, the extension cylinder is slided to extend the grip section and regulate a length according to the state of use. According to the invention as defined in claim 12, the cover cylinder is inserted in the holding hole of the urine taking cap to bring into the urine taking state.

In the assembled state, the examinee grips the grip body of the grip section of the urine taking cap or the extension cylinder with the blocking end side of the vessel body turned downward. The examinee passes urine over the urine sampling inlet. Consequently, the urine is injected from the urine sampling inlet into the vessel body. According to the invention as defined in claim 11, particularly, the urine is injected from one urine sampling inlet into the vessel body and is housed in the vessel body. Thus, the work of taking the urine is terminated. In that case, the urine and the grip section are severed by the ring protrusion according to the invention as defined in claim 9.

When the work of taking the urine is terminated, the vessel body is inserted in the cover cylinder up to the urine sampling cylinder section of the urine taking cap with the blocking end side of the vessel body turned downward. According to the invention as defined in claim 8, particularly, the opened end of the cover cylinder is caused to tightly come in contact with the tapered face to close the urine sampling inlet.

According to the invention as defined in claim 10, furthermore, the extension cylinder is pressed down to the ring protrusion of the urine taking cap to cover the grip body.

In the state in which the vessel body and the urine taking cap are inserted in the cover cylinder, they are inserted in the vessel holder or the like and carried to the examination room or the like.

Then, when performing the urinalysis, the urine taking cap is removed with the cover cylinder attached to the vessel body, and the vessel body is set on the examination apparatus to perform the urinalysis.

Furthermore, the reagent, the test paper or the like may be inserted through the opened end of the vessel body to perform the examination, or the reagent, the test paper or the like may be inserted through the urine sampling inlet with the urine taking cap attached to the vessel body to perform the examination.

-Effect-

According to the invention as defined in claim 1, consequently, the urine sampling inlets are formed on the vessel body comprising the cap and the vessel body can be covered with the cover cylinder. Therefore, the examinee only passes urine over the urine sampling inlets so that the urine can be taken when performing the urinalysis. As a result, the urine can be taken without spilling over hands and the like. Thus, the urine can be taken very sanitarily.

Since the vessel body and the cover cylinder are slender cylinders, they can be stood and kept by the vessel holder or the like after taking the urine. Consequently, a keeping space can be used efficiently.

When carrying the taken urine, the taken urine does not drop off because the vessel body is wholly covered with the cover cylinder. Consequently, the taken urine can be handled very sanitarily and easily.

Since the vessel body is blocked by the cap, a bad smell can surely be prevented from being generated. Therefore, examination work can be performed efficiently.

According to the invention as defined in claim 2, since the cover cylinder is held in the holding hole of the cap, the cover cylinder can be prevented from being lost and covering operation can be performed rapidly and easily after taking the urine.

According to the invention as defined in claim 3, the examination opening is provided on the vessel body. Consequently, the examination can also be performed by pulling out the cover cylinder during the examination. Therefore, the examination work can be performed easily.

According to the invention as defined in claim 4, the cap body is provided with the engagement groove in which the opened ends of the vessel body and the cover cylinder are inserted. Consequently, the opened end can surely be blocked when carrying the vessel. Thus, the urine can surely be prevented from leaking so that it can be handled sanitarily.

According to the invention as defined in claim 5, since the protrusion is formed on the outer peripheral face of the vessel body, the cover cylinder can surely be prevented from dropping off. Consequently, sanitation can be enhanced.

According to the invention as defined in claim 6, the flange section is formed on the cap body. Consequently, the urine can surely be prevented from spilling over hands and the like when taking the urine.

According to the invention as defined in claim 7, the urine sampling inlets are formed on the urine taking cap removably attached to the vessel body, and the vessel body and the urine sampling cylinder section of the urine taking cap can be covered with the cover cylinder. Consequently, the examinee only passes urine over the urine sampling inlets so that the urine can be taken when performing the urinalysis in the same manner as in the invention as defined in claim 1. As a result, the urine can be taken without spilling over hands and the like. Thus, the urine can be taken very sanitarily.

Since the vessel body and the cover cylinder are long cylinders, they can be stood and kept by the vessel holder or the like after taking the urine. Consequently, a keeping space can be used efficiently.

When carrying the taken urine, the taken urine does not leak because the vessel body and the urine sampling cylinder section of the urine taking cap are wholly covered with the cover cylinder. Consequently, the taken urine can be handled very sanitarily and easily.

Since the urine sampling inlets are closed by the cover cylinder, a bad smell can surely be prevented from being generated. Therefore, examination work can be performed efficiently.

Since the vessel body and the urine taking cap are inserted in the cover cylinder which is another member, the urine sampling inlets and the like can be covered without coming in contact with the vessel body and the like. Consequently, sealing work can be performed very sanitarily.

The urine sampling inlets and the like are not formed on the vessel body. Consequently, when centrifugalizing and examining the taken urine, it is not necessary to pour the urine into a vessel and the vessel body can exactly be applied to the examination apparatus. Thus, the examination can be performed rapidly.

According to the invention as defined in claim 8, since the tapered face is formed on the urine sampling cylinder section of the urine taking cap, the cover cylinder can tightly come in contact with the tapered face surely. Consequently, the urine sampling inlets and the like can surely be closed. Thus, the taken urine can surely be prevented from leaking.

According to the invention as defined in claim 9, since the ring protrusion is formed between the urine sampling cylinder section and the grip section, the grip section and the urine can surely be severed when taking the urine. Consequently, the urine can be taken very sanitarily without spilling over hands.

According to the invention as defined in claim 10, since the extension cylinder having a bottom or no bottom is fitted in the grip body of the grip section so as to be freely slided, the grip section can be extended according to the state of use. Consequently, the urine can be taken sanitarily without spilling over hands.

Even if the urine sticks to the grip body, the extension cylinder is pressed down after taking the urine so that the urine can be removed. Consequently, it is possible to completely take the urine without touching the urine.

According to the present invention as defined in claim 11, one urine sampling inlet is formed on the urine taking cap. Therefore, the urine taking cap can be easily molded and become inexpensive.

According to the invention as defined in claim 12, the cover cylinder is held in the holding hole of the urine taking cap. Consequently, the cover cylinder can be prevented from being lost, and covering operation can be performed rapidly and easily after taking the urine.

[BEST MODE FOR CARRYING OUT THE INVENTION]

Embodiments of the present invention will be described below in detail with reference to the drawings.
-Embodiment 1-

Figure 1:
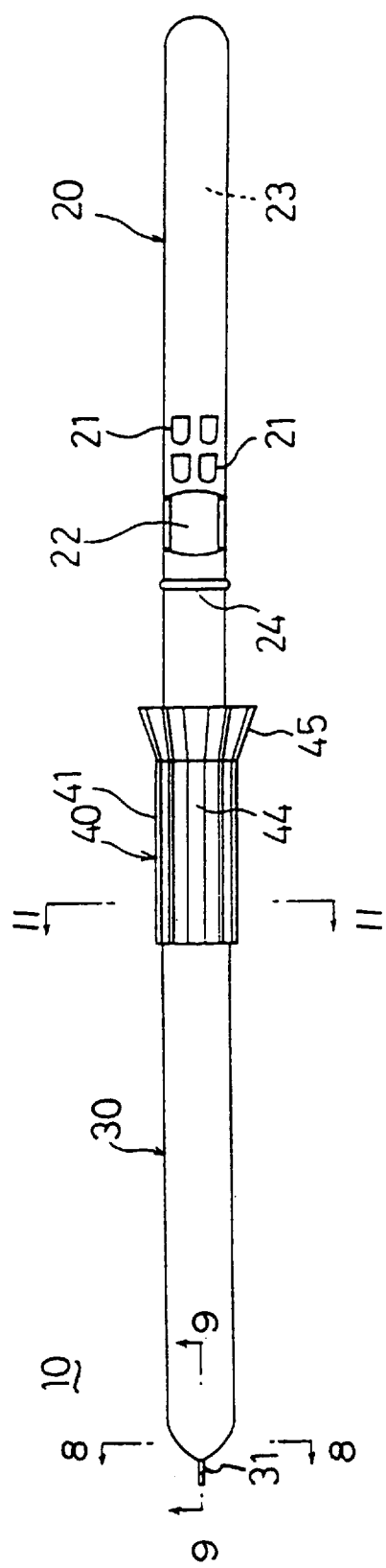
FIG. 1 is a front view showing a urine sampling vessel according to an embodiment 1.
Figure 2:
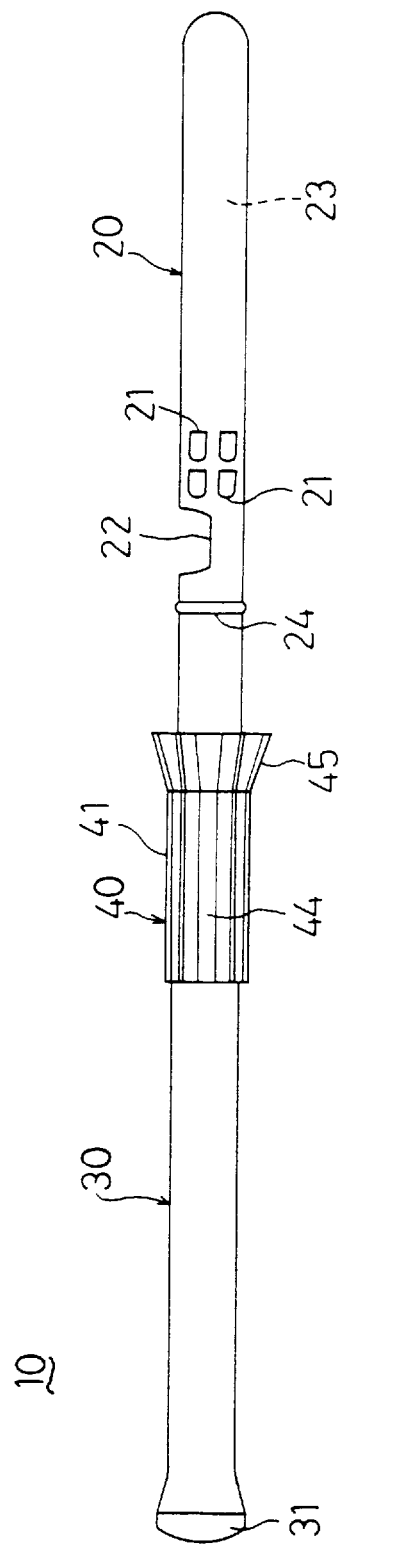
FIG. 2 is a plan view showing the urine sampling vessel according to the embodiment 1.
Figure 3:
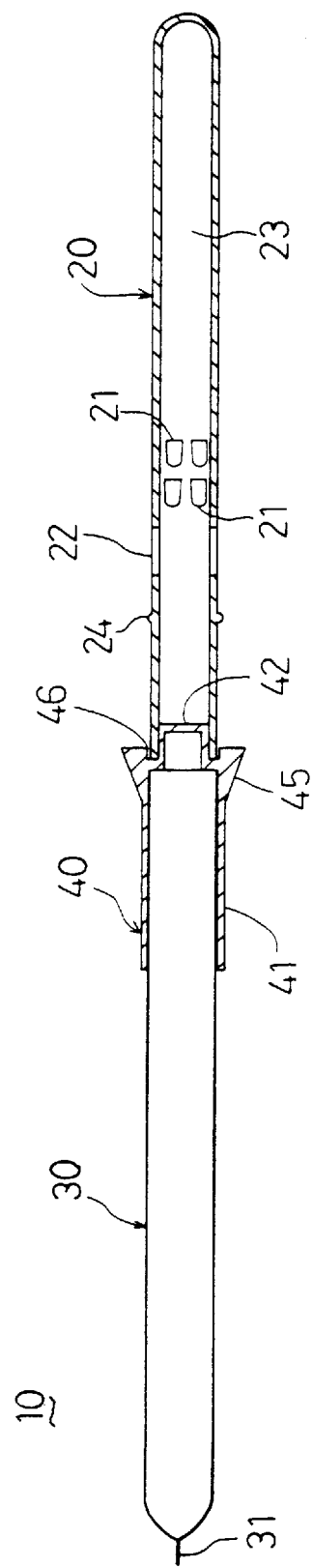
FIG. 3 is a longitudinally sectional view showing the urine sampling vessel according to the embodiment 1.

FIGS. 1 to 14 show an embodiment of the invention as defined in claims 1 to 6. As shown in FIGS. 1 to 3, a urine sampling vessel 10 is used for taking urine when performing a urinalysis in hospitals and the like.

The urine sampling vessel 10 comprises a vessel body 20 for housing taken urine, a cover cylinder 30 capable of covering the vessel body 20, and a cap 40 removably attached to the vessel body 20.

Figure 4:
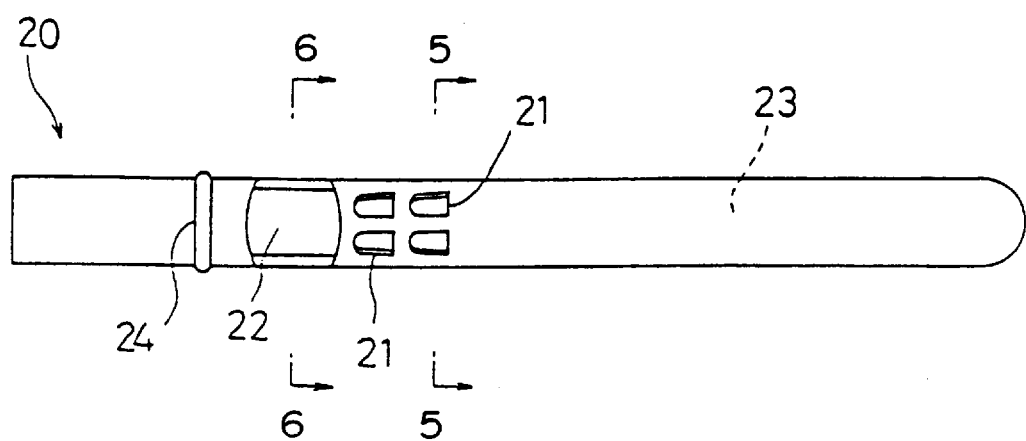
FIG. 4 is a front view showing a vessel body according to the embodiment 1.

As shown also in FIG. 4, the vessel body 20 has the shape of a slender cylinder having an end blocked and the other end opened, and more specifically, a cylinder having an outside diameter of 9.2 mm, an inside diameter of 7.2 to 6.6 mm and a length of 103 mm. The vessel body 20 is formed of a transparent material such as a synthetic resin.

Furthermore, the vessel body 20 has urine sampling inlets 21, 21, . . . and an examination opening 22 formed thereon, and has a urine housing section 23 formed from the urine sampling inlets 21, 21, . . . toward a blocking end side.

Figure 5:
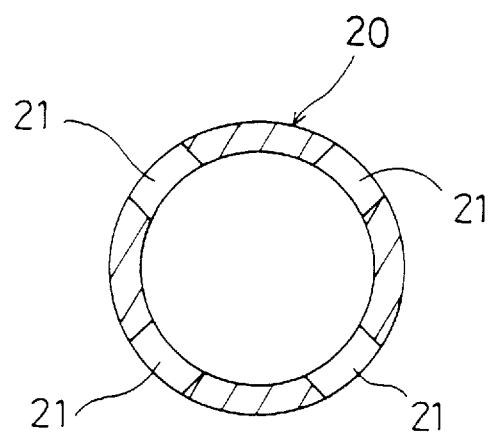
FIG. 5 is a sectional view taken along the line 5—5 shown in FIG. 4 according to the embodiment 1.

As shown in FIG. 5, the urine sampling inlets 21, 21, . . . are openings in which urine is injected when taking the urine, and are formed four by four in two steps in an almost central portion in a longitudinal direction of the vessel body 20, that is, the total number thereof is eight. The urine sampling inlets 21, 21, . . . are formed at regular intervals in a circumferential direction of the vessel body 20, and are formed like a semiellipse having a length of 4 mm in the longitudinal direction, for example.

Figure 6:
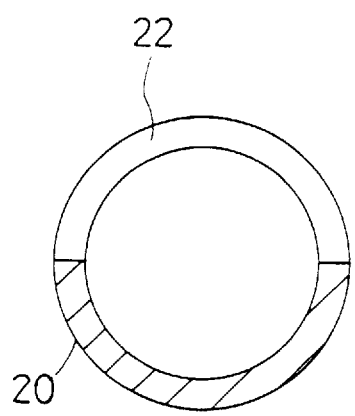
FIG. 6 is a sectional view taken along the line 6—6 shown in FIG. 4 according to the embodiment 1.

The examination opening 22 causes a test paper for an examination or the like to be inserted therein when performing the urinalysis, and is positioned from the urine sampling inlets 21, 21, . . . toward an opened end side and is one in number. The examination opening 22 is formed by cutting out a part of an upper half portion of the vessel body 20 as shown in FIGS. 2 and 6, and is provided in the form of an opening having a length of 10 mm in the longitudinal direction, for example.

Figure 12:
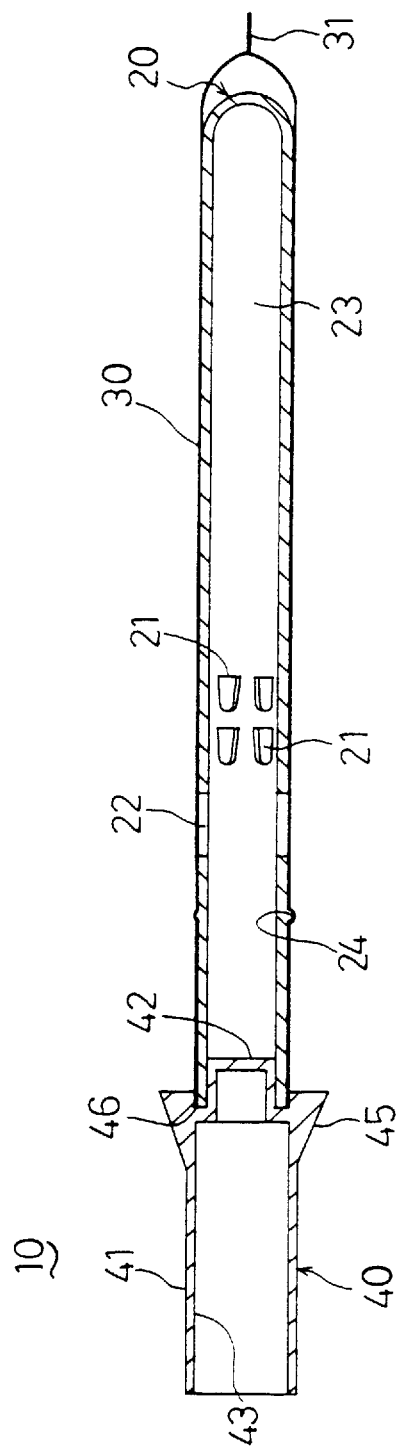
FIG. 12 is a longitudinally sectional view showing the urine sampling vessel in the state obtained after taking urine according to the embodiment 1.

A ring protrusion 24 is formed on an outer peripheral face on the opened end side of the vessel body 20. As shown in FIG. 12, a cover cylinder 30 is attached to the protrusion 24 by pressure when putting on the cover cylinder 30 such that the cover cylinder 30 does not drop off easily.

Figure 7:
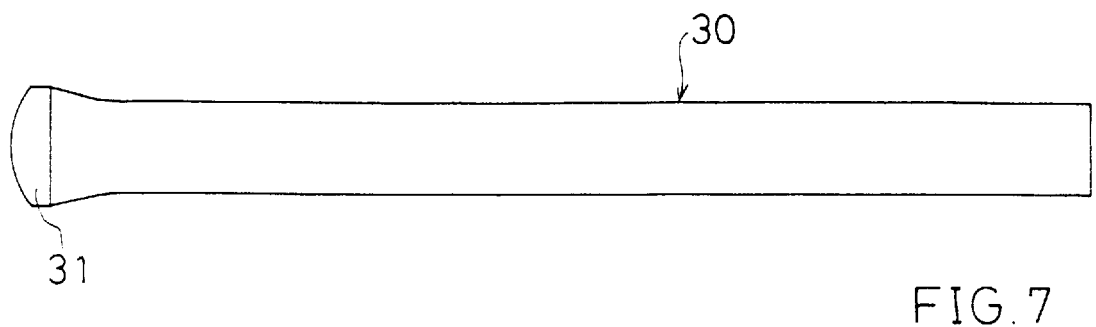
FIG. 7 is a plan view showing a cover cylinder according to the embodiment 1.

As shown also in FIG. 7, the cover cylinder 30 has the shape of a slender cylinder having an end blocked and the other end opened, and causes the vessel body 20 to be freely inserted in tight contact therewith and pulled out thereof. More specifically, the cover cylinder 30 has the shape of a cylinder having an outside diameter of 10.1 mm, an inside diameter of 9.5 mm and a length of 106 mm, for example, and has such a length that the urine sampling inlets 21, 21, . . . and the examination opening 22 are closed when inserting the vessel body 20 in the cover cylinder 30 as shown in FIG. 12.

The cover cylinder 30 is formed of a thinly flexible material such as a synthetic resin, and is transparent or translucent. More specifically, the cover cylinder 30 is formed such that discoloration of a test paper or the like can be recognized from the outside when inserting the test paper or the like in the vessel body 20.

Figure 8:
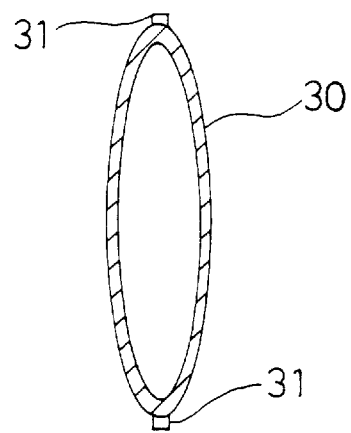
FIG. 8 is a sectional view taken along the line 8—8 shown in FIG. 1 according to the embodiment 1.
Figure 9:
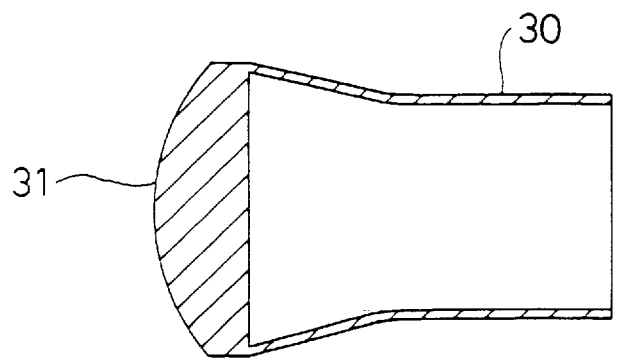
FIG. 9 is a sectional view taken along the line 9—9 shown in FIG. 1 according to the embodiment 1.

Furthermore, a blocking end 31 of the cover cylinder 30 is formed to thermally fuse and block the opened end as shown in FIGS. 8 and 9.

Figure 10:
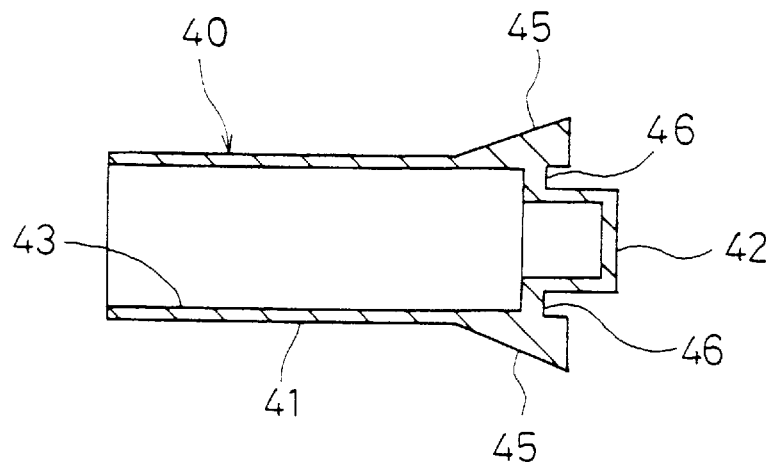
FIG. 10 is a longitudinally sectional view showing a cap according to the embodiment 1.
Figure 11:
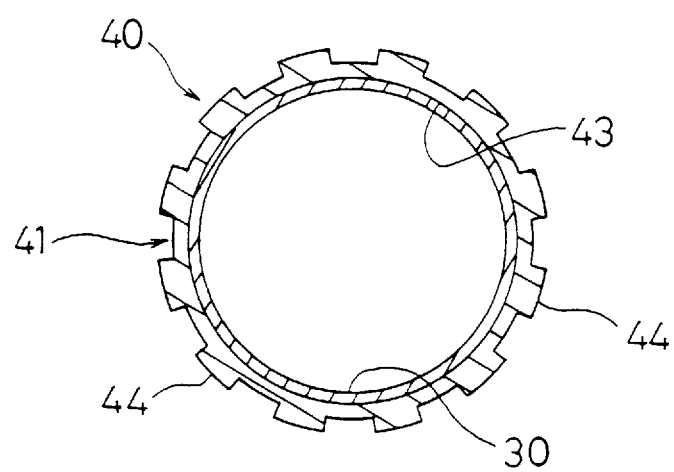
FIG. 11 is a sectional view taken along the 11—11 shown in FIG. 1 according to the embodiment 1.

As shown also in FIGS. 10 and 11, the cap 40 closes the opened end of the vessel body 20 and also serves as a grip section, and includes a cap body 41 having a blocking plug section 42 and a holding hole 43 formed thereon.

The cap body 41 is formed almost like a cylinder having a length of 30.5 mm, for example, and has nonslip knurling notches 44 formed in the longitudinal direction and has a flange section 45 which extends to the outside toward an end face side of the blocking plug section 42.

The blocking plug section 42 has the shape of a short column which can be freely inserted in pressure contact with the inside of the opened end of the vessel body 20 and pulled out thereof, and is formed so as to close the opened end of the vessel body 20.

The holding hole 43 is opened on an end face of the cap body 41 and is formed such that the opened end of the cover cylinder 30 can be freely inserted therein and removed therefrom, and has a depth of 29 mm, for example.

In addition, the cap body 41 has an engagement groove 46 formed in connection to an outer periphery of a base end of the blocking plug section 42 and causing the opened ends of the vessel body 20 and the cover cylinder 30 to be inserted with the vessel body 20 inserted in the cover cylinder 30. The engagement groove 46 is formed so as to seal the opened ends of the vessel body 20 and the cover cylinder 30 when carrying the vessel.

-Method for Using the Urine Sampling Vessel 10 according to Embodiment 1-

A method for using the urine sampling vessel 10 will be described below.

First of all, the vessel body 20, the cover cylinder 30 and the cap 40 of the urine sampling vessel 10 are housed separately in a case or the like before taking urine. When taking the urine, the cap 40 is attached to the opened end of the vessel body 20 at the blocking plug section 42, and the cover cylinder 30 is inserted and held in the holding hole 43 of the cap 40. Thus, the urine sampling vessel 10 is assembled to be brought into the urine taking state as shown in FIGS. 1 and 2.

In the assembled state, the examinee grips the cap 40 with the blocking end side of the vessel body 20 turned downward. The examinee passes urine over the urine sampling inlets 21, 21, . . . so that the urine is injected from the urine sampling inlets 21, 21, . . . into the vessel body 20 and is then housed in the housing section 23 of the vessel body 20. Thus, the work of taking the urine is terminated.

When the work of taking the urine is terminated, the cover cylinder 30 is pulled out of the cap 40 with the blocking end side of the vessel body 20 turned downward, and the vessel body 20 is inserted in the cover cylinder 30. By putting the cover cylinder 30 on the vessel body 20, the urine sampling inlets 21, 21, . . . and the examination opening 22 are closed, the opened ends of the cover cylinder 30 and the vessel body 20 are inserted in the engagement groove 46 of the cap 40 so that the both opened ends are blocked, and the ring protrusion 24 of the vessel body 20 tightly comes in contact with the cover cylinder 30 to obtain non-slip as shown in FIG. 12.

In the state in which the vessel body 20 is inserted in the cover cylinder 30, they are inserted in a vessel holder or the like and carried to an examination room or the like.

Figure 13:
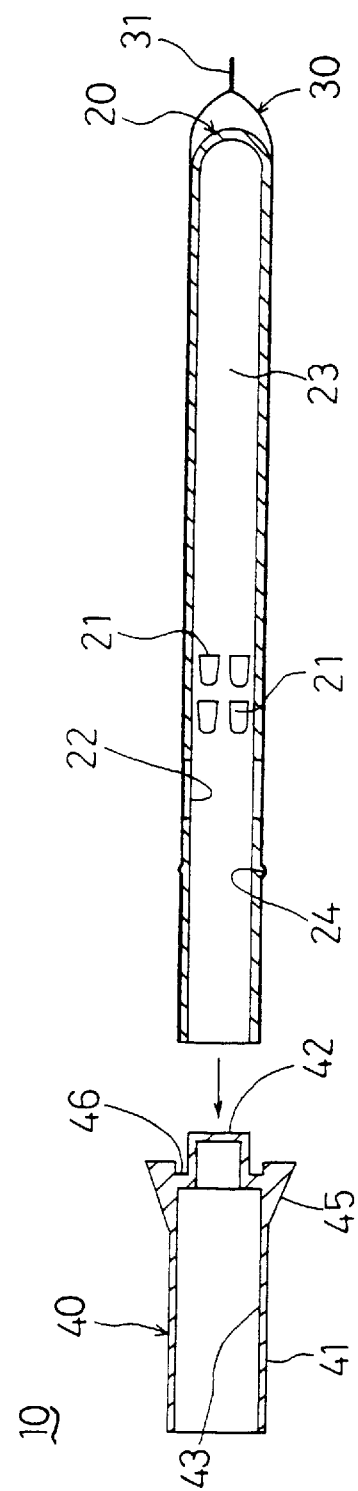
FIG. 13 is a longitudinally sectional view showing the urine sampling vessel during a urinalysis according to the embodiment 1.

As shown in FIG. 13, when performing the urinalysis, the cap 40 is then removed with the vessel body 20 inserted in the cover cylinder 30, and a reagent, a test paper or the like is inserted through the opened end of the vessel body 20 to perform the urinalysis.

Figure 14:
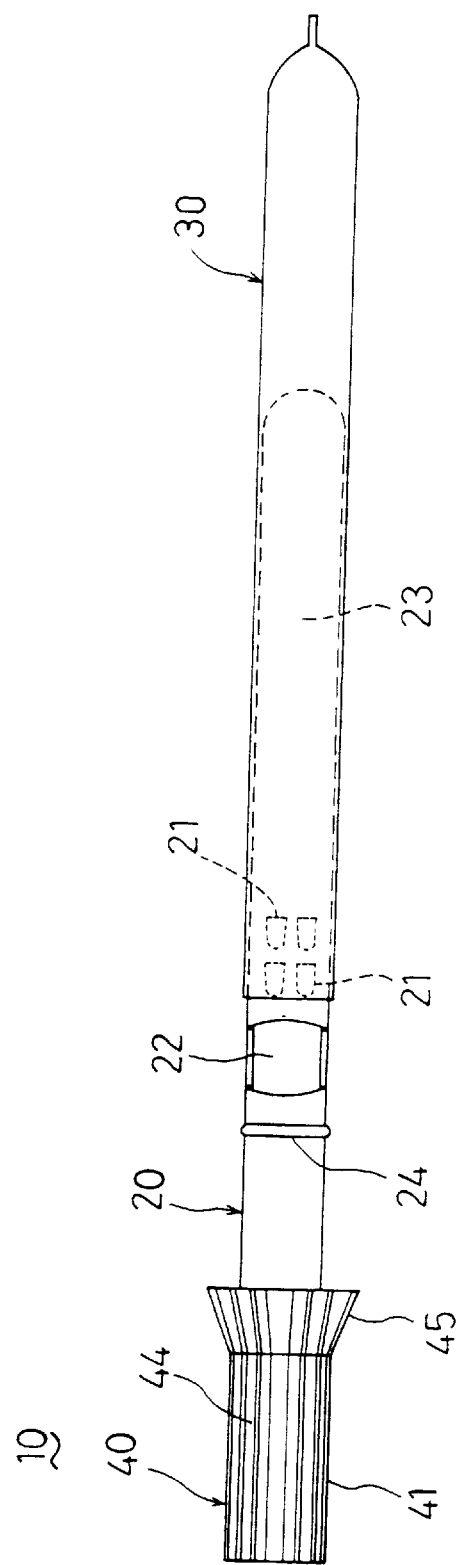
FIG. 14 is a front view showing the urine sampling vessel during another urinalysis according to the embodiment 1.

As shown in FIG. 14, the cover cylinder 30 is slightly pulled out of the vessel body 20 with the cap 40 attached to the vessel body 20 so that only the examination opening 22 is opened. The reagent, the test paper or the like is inserted through the examination opening 22 to perform the examination.

-Peculiar Effect of the Urine Sampling Vessel 10 according to Embodiment 1-

According to the present embodiment, consequently, the urine sampling inlets 21, 21, . . . are formed on the vessel body 20 comprising the cap 40 and the vessel body 20 can be covered with the cover cylinder 30. Therefore, the examinee only passes urine over the urine sampling inlets 21, 21, . . . so that the urine can be taken when performing the urinalysis. As a result, the urine can be taken without spilling over hands and the like. Thus, the urine can be taken very sanitarily.

Since the vessel body 20 and the cover cylinder 40 are slender cylinders, they can be stood and kept by the vessel holder or the like after taking the urine. Consequently, a keeping space can be used efficiently.

When carrying the taken urine, the taken urine does not spill because the vessel body 20 is wholly covered with the cover cylinder 30. Consequently, the taken urine can be handled very sanitarily and easily.

Since the vessel body 20 is blocked by the cap 40, a bad smell can surely be prevented from being generated. Therefore, examination work can be performed efficiently.

Since the cover cylinder 30 is held in the, holding hole 43 of the cap 40, the cover cylinder 30 can be prevented from being lost and covering operation can be performed rapidly and easily after taking the urine.

The examination opening 22 is provided on the vessel body 20. Consequently, the examination can also be performed by pulling out the cover cylinder 30 during the examination. Therefore, the examination work can be performed easily.

The cap body 41 has the engagement groove 46 formed thereon, in which the opened ends of the vessel body 20 and the cover cylinder 30 are caused to be inserted. Consequently, the opened end can surely be blocked when carrying the vessel. Thus, the urine can surely be prevented from leaking so that it can be handled sanitarily.

Since the protrusion 24 is formed on the outer peripheral face of the vessel body 20, the cover cylinder 30 tightly comes in contact so that the cover cylinder 30 can surely be prevented from dropping off. Consequently, sanitation can be enhanced.

The flange section 45 is formed on the cap body 41. Consequently, the urine can surely be prevented from spilling over hands and the like when taking the urine.

-Embodiment 2-

Figure 15:
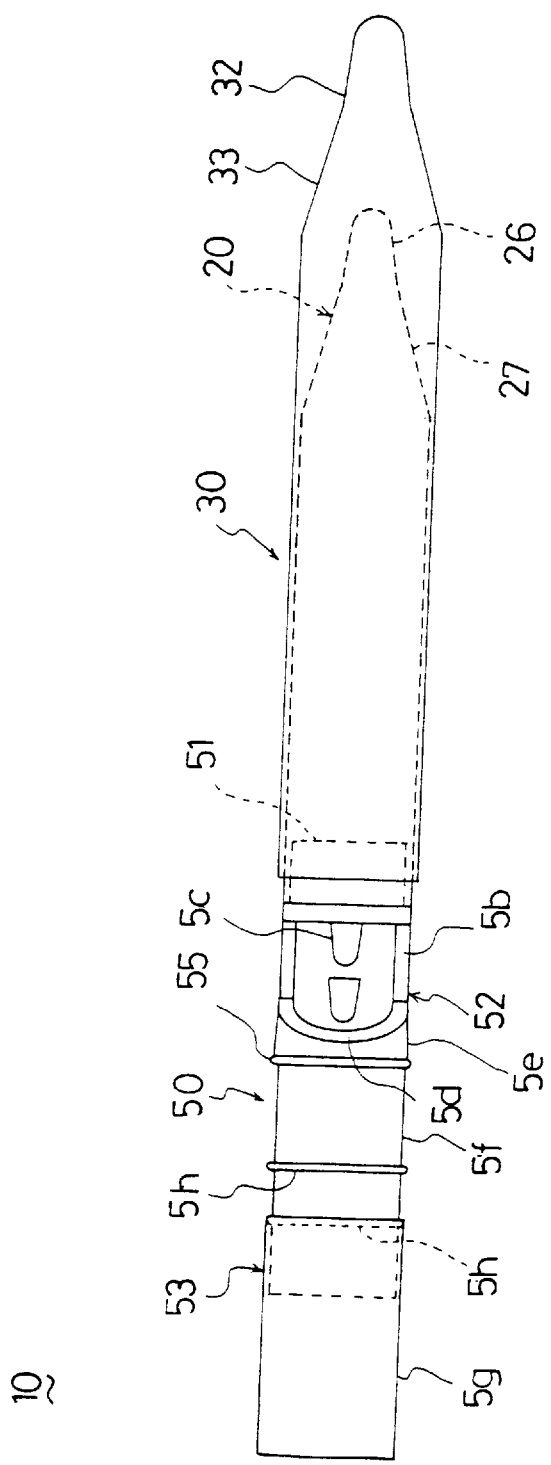
FIG. 15 is a front view showing a urine sampling vessel according to an embodiment 2.

FIGS. 15 to 21 show an embodiment of the invention as defined in claims 7 to 10. As shown in FIG. 15, a urine sampling vessel 10 has a greater diameter than that of the urine sampling vessel 10 according to the embodiment 1, and can also serve as a sample vessel of an examination apparatus.

The urine sampling vessel 10 comprises a vessel body 20 for housing the taken urine, a urine taking cap 50 removably attached to the vessel body 20, and a cover cylinder 30 for covering the vessel body 20 and a part of the urine taking cap 50.

Figure 16:
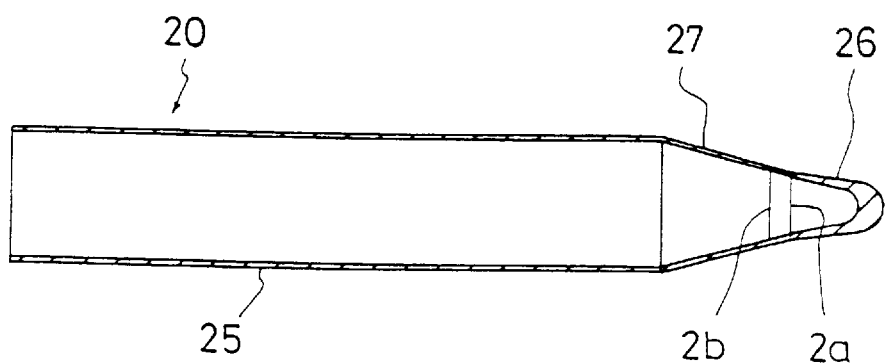
FIG. 16 is a longitudinally sectional view showing a vessel body according to the embodiment 2.

As shown in FIG. 16, the vessel body 20 has an end blocked and the other end opened, has a body section 25 in the form of a slender cylinder, and has a greater diameter than that of the vessel body 20 according to the embodiment 1. More specifically, the vessel body 20 has an outside diameter of 15.6 to 14.7 mm and an inside diameter of 14.0 to 13.1 mm, for example, and has the shape of a cylinder having a total length of 87 mm. The vessel body 20 is formed of a transparent material such as a synthetic resin.

A first reducing section 26 and a second reducing section 27 are formed on a tip portion of the vessel body 20. The first reducing section 26 is formed like a taper which extends from a blocking end on a tip toward the second reducing section 2, and is connected to the second reducing section 27 through a first fold. The second reducing section 27 is formed like a taper which extends toward the body section 25, and has a greater inclination of the taper than that of the first reducing section 26 and is connected to the body section 25 through a second fold.

The first fold is formed on a first marked line 2a, and a second marked line 2b is indicated with a micro step difference on the second reducing section 27 from the first marked line 2a toward a body section 25 side. The first marked line 2a and the second marked line 2b indicate amounts of urine remaining after centrifugalizing and skimming the taken urine to get a sample for a unitary sediment examination (25 μl; microliter), and are set to display storage amounts of 0.1 cc and 0.2 cc, respectively.

Figure 17:
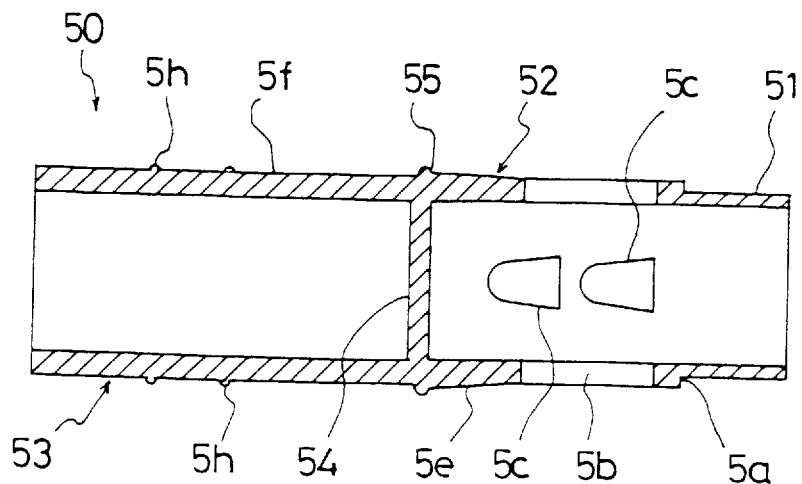
FIG. 17 is a longitudinally sectional view showing a urine taking cap according to the embodiment 2.
Figure 18:
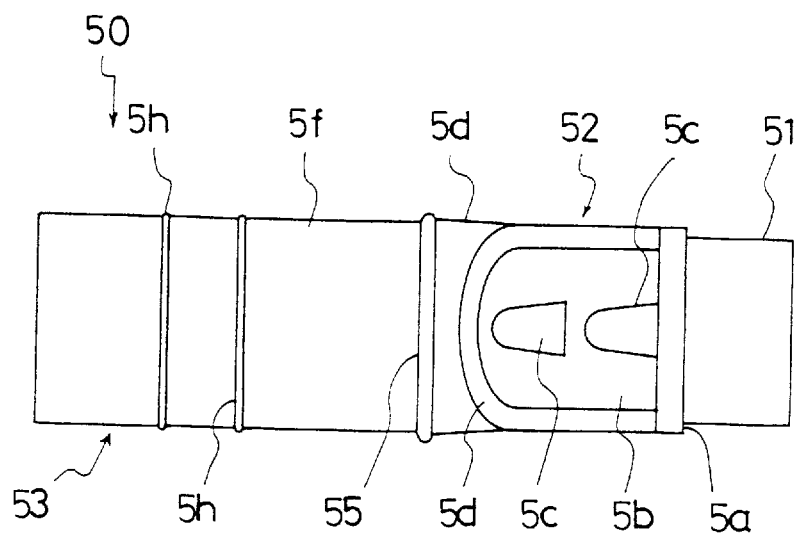
FIG. 18 is a front view showing the urine taking cap according to the embodiment 2.
Figure 19:
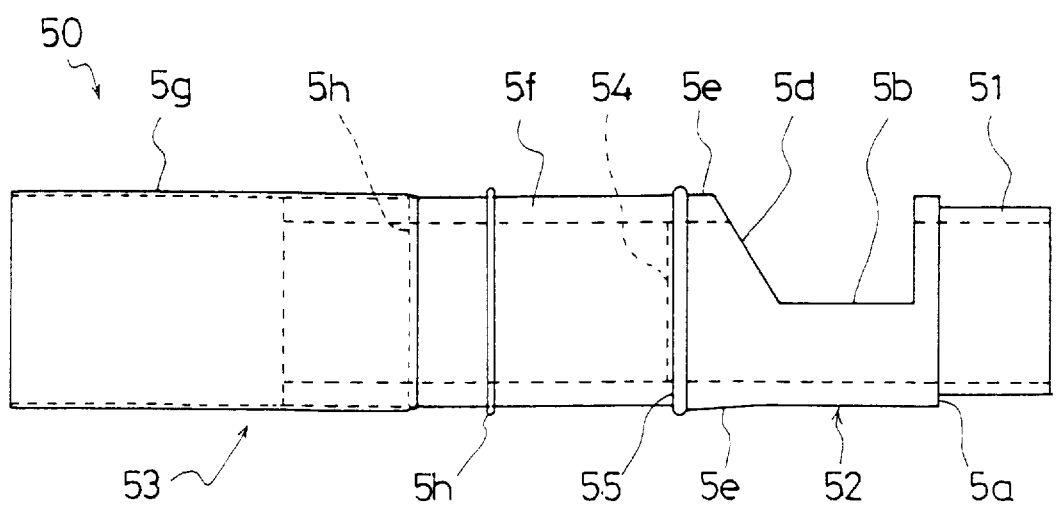
FIG. 19 is a plan view showing the urine taking cap according to the embodiment 2.

The urine taking cap 50 is a cylinder having a fitting cylinder section 51, a urine sampling cylinder section 52 and a grip section 53 continuously provided in order from an inner end on a vessel body 20 side toward an outer end as shown in FIGS. 17 to 19, and is formed of a colored synthetic resin material.

The fitting cylinder section 51 is formed so as to be freely fitted in the opening end of the vessel body 20, and has a hollow shape whose both ends are opened. More specifically, the fitting cylinder section 51 has an outside diameter of 14.4 mm and a length of 8 mm, for example.

The urine sampling cylinder section 52 is formed like a cylinder having a bottom which is connected to the fitting cylinder section 51 through a step difference face 5a, and has an outer end side (a left end shown in FIG. 17) blocked. A bottom portion forms a blocking wall 54 which blocks the outer end of the urine sampling cylinder section 52. The urine sampling cylinder section 52 has almost the same outside diameter as that of the vessel body 20 and has a length of 27 mm, for example, and is provided with a first urine sampling inlet 5b and a second urine sampling inlet 5c.

The both urine sampling inlets 5b and 5c are openings into which the urine is injected when taking the urine and are positioned from the blocking wall 54 toward an inner end side (a right end shown in FIG. 17) of the urine sampling cylinder section 52, and penetrate from an outer peripheral face of the urine sampling cylinder section 52 to an inner peripheral face thereof.

The first urine sampling inlet 5b is formed by cutting out a part of an upper half portion of the urine sampling cylinder section 52 in a circumferential direction, and is an opening having an axial length of 15 mm, for example, and its rear end face is formed as a slope 5d which rises toward the grip section 53 as seen on a plane in FIG. 19.

Two second urine sampling inlets 5c are axially formed in series in a lower half portion of the urine sampling cylinder section 52 opposite to the first urine sampling inlet 5b, and have the shape of a semiellipse having an axial length of 4 mm, for example. The reason why the second urine sampling inlets 5c are formed is that ventilating function is performed when taking the urine so as to easily take the urine and prevent deformation during forming.

An outer peripheral face on a rear end of the urine sampling cylinder section 52 (the outer peripheral face on a grip section 53 side) is formed as a tapered face 5e whose diameter is increased toward the rear end. When putting on the cover cylinder 30 to be described below, the cover cylinder 30 tightly comes in contact with and is fitted in the outer peripheral face so that the cover 30 is not easily pulled out.

The grip section 53 is connected to the outer end of the urine sampling cylinder section 52, and comprises a grip body 5f and an extension cylinder 5g. The grip body 5f has the shape of a hollow cylinder having both ends opened.

A ring protrusion 55 for severing the grip section 53 and the taken urine is formed on an outer peripheral face of a connecting portion of the grip section 53 and the urine sampling cylinder section 52.

The extension cylinder 5g having a bottom is fitted in the grip body 5f so as to be freely slided such that the grip section 53 is freely extended axially. The grip body 5f has a length of 34.5 mm, for example, and has two ribs 5h, 5h formed at predetermined intervals on an outer peripheral face thereof. The extension cylinder 5g has a length of 60 mm, for example, and has a slightly projecting inward flange formed on an inner end thereof, which is not shown. The flange of the extension cylinder 5g engages with the ribs 5h, 5h and can be held by the grip body 5f in two extended positions. As a matter of course, the extension cylinder 5g may have no bottom and may have no inward flange formed thereon.

Figure 20:
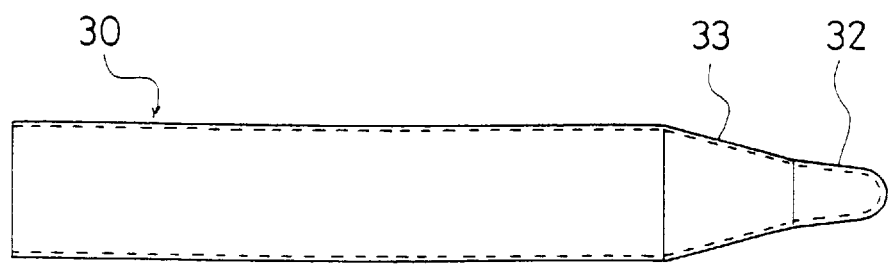
FIG. 20 is a front view showing a cover cylinder according to the embodiment 2.

As shown in FIG. 20, the cover cylinder 30 has an end blocked and the other end opened, and has the shape of a slender cylinder similar to the vessel body 20 so as to cause the vessel body 20 to be freely inserted therein and pulled out thereof. More specifically, the cover cylinder 30 has the shape of a cylinder having an outside diameter of 16.5 mm, an inside diameter of 15.9 mm and a length of 107 mm, for example, and has a first reducing section 32 and a second reducing section 33 formed on a tip portion thereof.

The cover cylinder 30 is formed of a thinly flexible material such as a synthetic resin, and is transparent or translucent. As shown in FIG. 15, the cover cylinder 30 is formed to have such a length that the both urine sampling inlets 5b, 5c of the urine taking cap 50 are closed when inserting the vessel body 20 therein, and an opened end thereof tightly comes in contact with and is fitted in the tapered face 5e of the urine sampling cylinder section 52 during covering as shown in FIG. 15.

-Method for Using the Urine Sampling Vessel 10 according to Embodiment 2-

A method for using the urine sampling vessel 10 will be described below.

Figure 21:
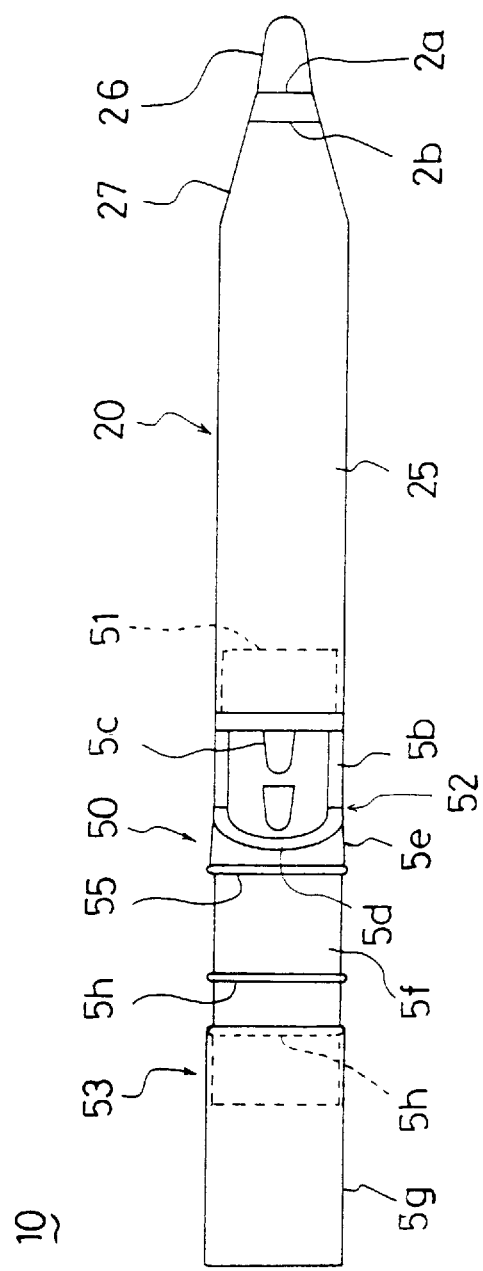
FIG. 21 is a front view showing the urine sampling vessel in the state in which urine is taken according to the embodiment 2.
Figure 22:
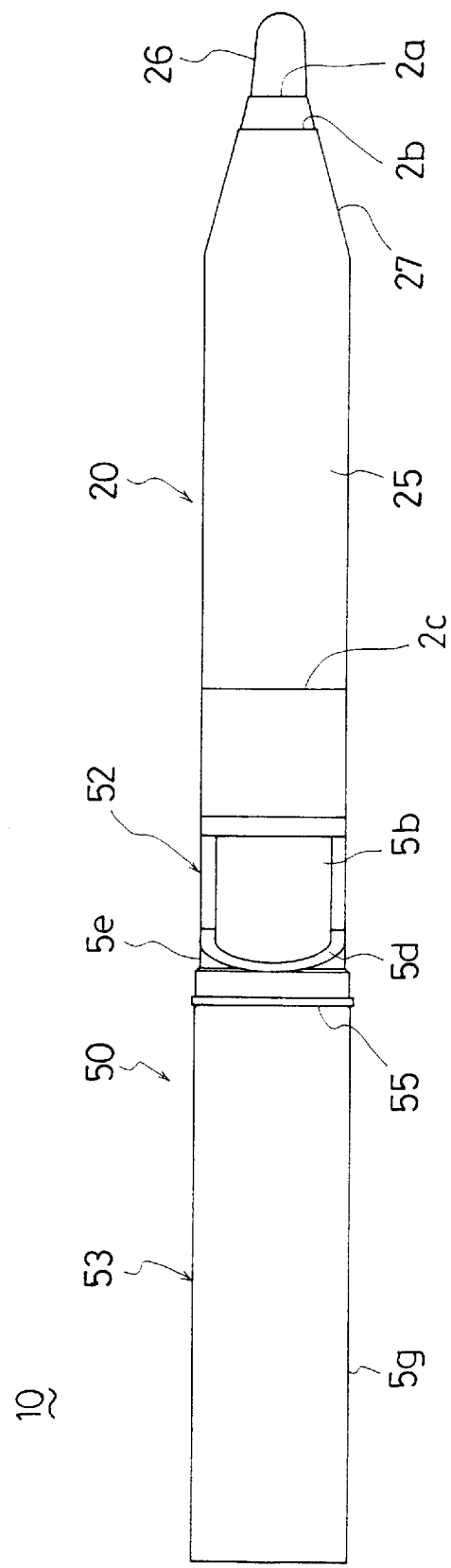
FIG. 22 is a front view showing a urine sampling vessel according to an embodiment 3.

When taking urine, the urine taking cap 50 is attached to the opened end of the vessel body 20 at the fitting cylinder section 51 and is brought into the urine taking state as shown in FIG. 21. The extension cylinder 5g of the grip section 53 is slided to regulate a length of the grip section 53 according to the state of use.

In the assembled state, the examinee grips the grip body 5f of the urine taking cap 50 or the slided extension cylinder 5g with the blocking end side of the vessel body 20 turned downward. The examinee passes urine over the first urine sampling inlet 5b. Consequently, the urine is injected from the first urine sampling inlet 5b into the vessel body 20, and is housed in the vessel body 20. Thus, the work of taking the urine is terminated.

When the work of taking the urine is terminated, the vessel body 20 is inserted in the cover cylinder 30 up to the urine sampling cylinder section 52 of the urine taking cap 50 with the blocking end side of the vessel body 20 turned downward, and the opened end of the cover cylinder 30 is caused to tightly come in contact with the tapered face 5e to close both urine sampling inlets 5b and 5c.

In that case, the extension cylinder 5g is simultaneously pressed down to the ring protrusion 55 of the urine taking cap 50 to cover the grip body 5f.

In the state in which the vessel body 20 and the urine taking cap 50 are inserted in the cover cylinder 30, they are inserted in a vessel holder or the like and carried to an examination room or the like.

Then, when performing the urinalysis, the urine taking cap 50 is removed with the cover cylinder 30 attached to the vessel body 20, and the vessel body 20 is set on the examination apparatus to perform the urinalysis.

A reagent, a test paper or the like may be inserted through the opened end of the vessel body 20 to perform the examination, or the reagent, the test paper or the like may be inserted through the first urine sampling inlet 5b with the urine taking cap 50 attached to the vessel body 20 to perform the examination.

-Peculiar Effect of the Urine Sampling Vessel 10 according to Embodiment 2-

According to the present embodiment described above, the first urine sampling inlet 5b and the second urine sampling inlet 5c are formed on the urine taking cap 50 removably attached to the vessel body 20, and the vessel body 20 and the urine sampling cylinder section 52 of the urine taking cap 50 can be covered with the cover cylinder 30. Consequently, the examinee only passes urine over the urine sampling inlets 5b, 5c so that the urine can be taken when performing the urinalysis. As a result, the urine can be taken without spilling over hands and the like. Thus, the urine can be taken very sanitarily.

Since the vessel body 20 and the cover cylinder 30 are slender cylinders, they can be stood and kept by the vessel holder or the like after taking the urine. Consequently, a keeping space can be used efficiently.

When carrying the taken urine, the taken urine does not leak because the vessel body 20 and the urine sampling cylinder section 52 of the urine taking cap 50 are wholly covered with the cover cylinder 30. Consequently, the taken urine can be handled very sanitarily and easily.

Since the both urine sampling inlets 5b, 5c are closed by the cover cylinder 30, a bad smell can surely be prevented from being generated. Therefore, examination work can be performed efficiently.

Since the vessel body 20 and the urine taking cap 50 are inserted in the cover cylinder 30 which is another member, the both urine sampling inlets 5b, 5c and the like can be covered without coming in contact with the vessel body 20 and the like. Consequently, inserting and sealing work can be performed very sanitarily.

The urine sampling inlets and the like are not formed on the vessel body 20. Consequently, when centrifugalizing and examining the taken urine, it is not necessary to pour the urine into a vessel and the vessel body 20 can exactly be applied to the examination apparatus. Thus, the examination can be performed rapidly.

Since the tapered face 5e is formed on the urine sampling cylinder section 52 of the urine taking cap 50, the cover cylinder 30 can tightly come in contact with the tapered face 5e surely. Consequently, the both urine sampling inlets 5b, 5c can surely be closed. Thus, the taken urine can surely be prevented from leaking.

Since the ring protrusion 55 is formed between the urine sampling cylinder section 52 and the grip section 53, the grip section 53 and the urine can surely be severed when taking the urine. Consequently, the urine can be taken sanitarily without spilling over hands.

Since the extension cylinder 5g having a bottom or no bottom is fitted in the grip body 5f of the grip section 53 so as to be freely slided, the grip section 53 can be extended according to the state of use. Consequently, the urine can be taken sanitarily without spilling over hands.

Even if the urine sticks to the grip body 5f, the extension cylinder 5g is pressed down to the ring protrusion 55 after taking the urine so that the urine can be removed. Consequently, it is possible to completely take the urine without touching the urine.

-Embodiment 3-

FIGS. 22 to 26 show an embodiment of the invention as defined in claim 11 which is a variant of the embodiment 2.

The present embodiment is the most different from the embodiment 2 in that only a first urine sampling inlet 5b is formed on a urine taking cap 50 and a second urine sampling inlet 5c is not formed.

More specifically, only one urine sampling inlet 5b is formed on a urine sampling cylinder section 52 in the urine taking cap 50 by cutting out a part of an upper half portion of the urine sampling cylinder section 52 in a circumferential direction.

Figure 24:
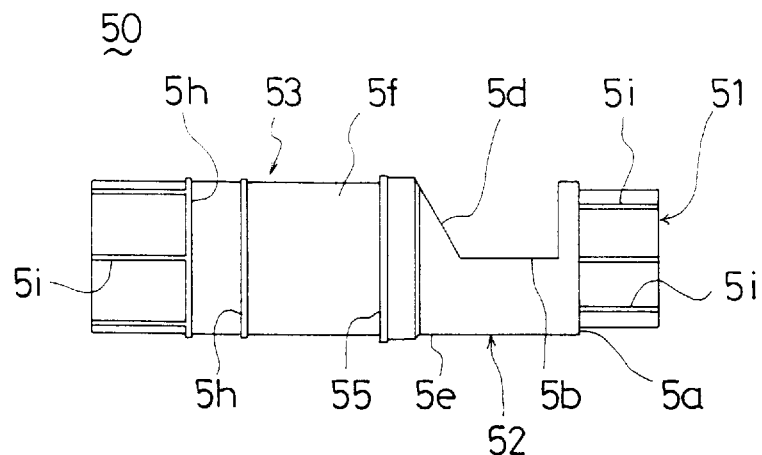
FIG. 24 is a plan view showing a urine taking cap according to the embodiment 3.
Figure 25:
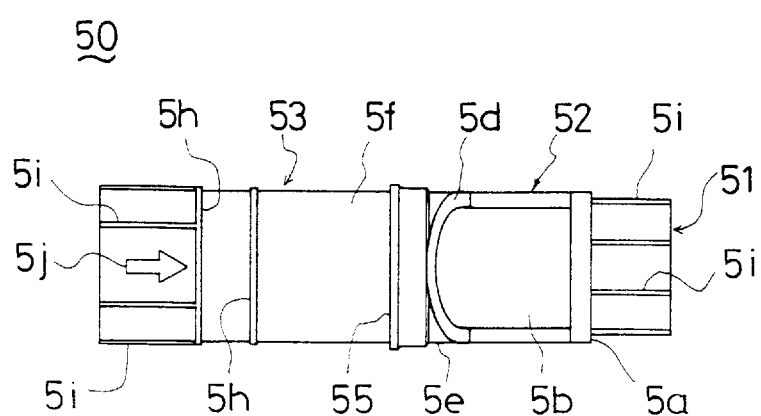
FIG. 25 is a front view showing the urine taking cap according to the embodiment 3.
Figure 26:
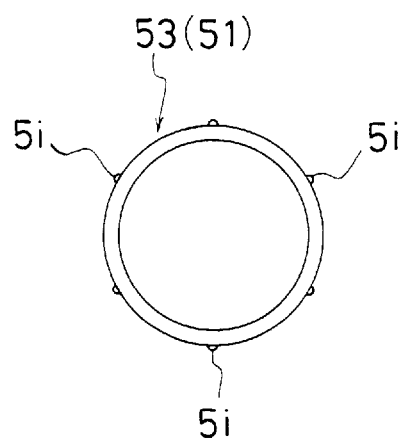
FIG. 26 is a side view showing the urine taking cap according to the embodiment 3.

As shown in FIGS. 24 to 26, the urine taking cap 50 is provided with projection parts 5i, 5i, . . . which are formed on a fitting cylinder section 51 and a grip body 5f.

Six projection parts 5i, 5i, . . . of the fitting cylinder section 51 are axially formed on an outer peripheral face of the fitting cylinder section 51 so as to easily insert and remove a vessel body 20. Six projection parts 5i, 5i, . . . of the grip body 5f are axially formed on an outer peripheral face of the grip body 5f from an outer rib 5h toward an outer end so as to easily slide an extension cylinder 5g.

Furthermore, an arrow 5j is formed on an outer end of the grip body 5f by piercing the grip body 5f. The arrow 5j makes a position of the urine sampling inlet 5b precise.

Figure 23:
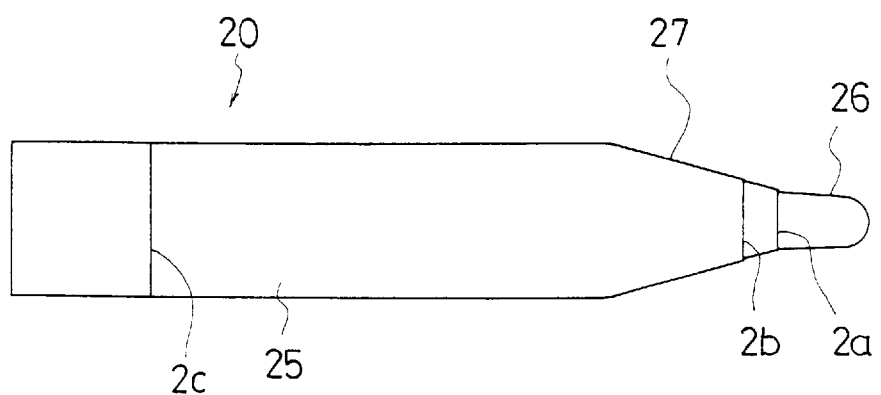
FIG. 23 is a front view showing a vessel body according to the embodiment 3.

On the other hand, a first marked line 2a and a second marked line 2b of the vessel body 20 are displayed precisely by a step difference as shown in FIG. 23.

In addition, a third marked line 2c is formed by a step difference on an opened end side of the vessel body 20, and serves to display an amount of taken urine necessary for a unitary sediment examination and is set to indicate a storage amount of 10 cc.

Other structures and functions are the same as in the embodiment 2.

According to the present embodiment, consequently, one urine sampling inlet 5b is formed on the urine taking cap 50. Therefore, the urine taking cap 50 can be easily molded and become inexpensive.

The operation of inserting and removing the vessel body 20 and that of sliding the extension cylinder 5g can be easily performed by the projection parts 5i, 5i, . . . . Consequently, it is easy to take the urine and perform a urinalysis.

Other effects are the same as in the embodiment 2.

-Embodiment 4-

Figure 27:
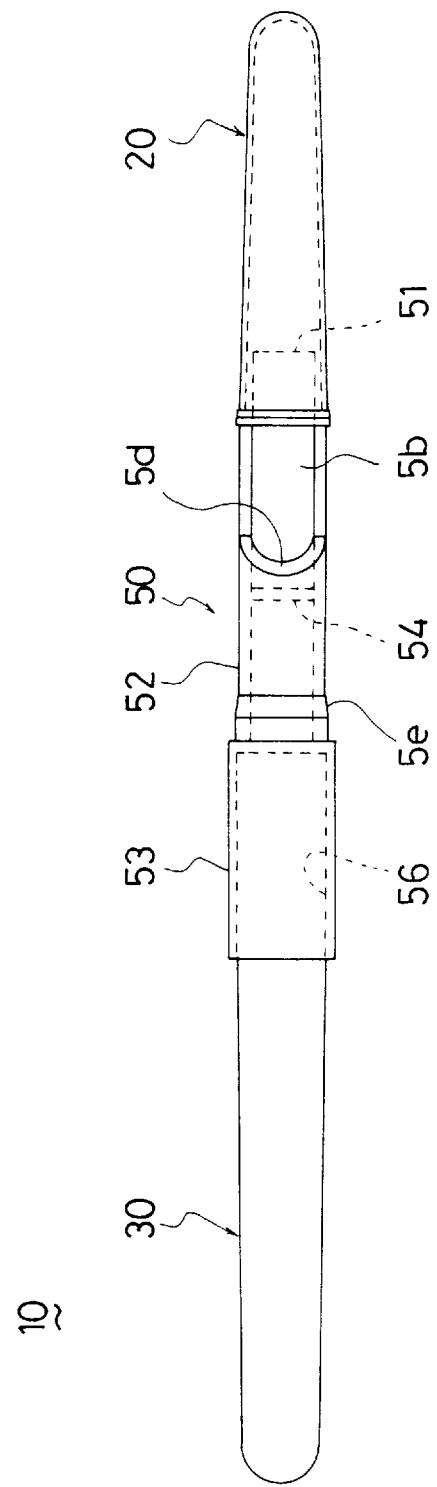
FIG. 27 is a front view showing a urine sampling vessel according to an embodiment 4.
Figure 28:
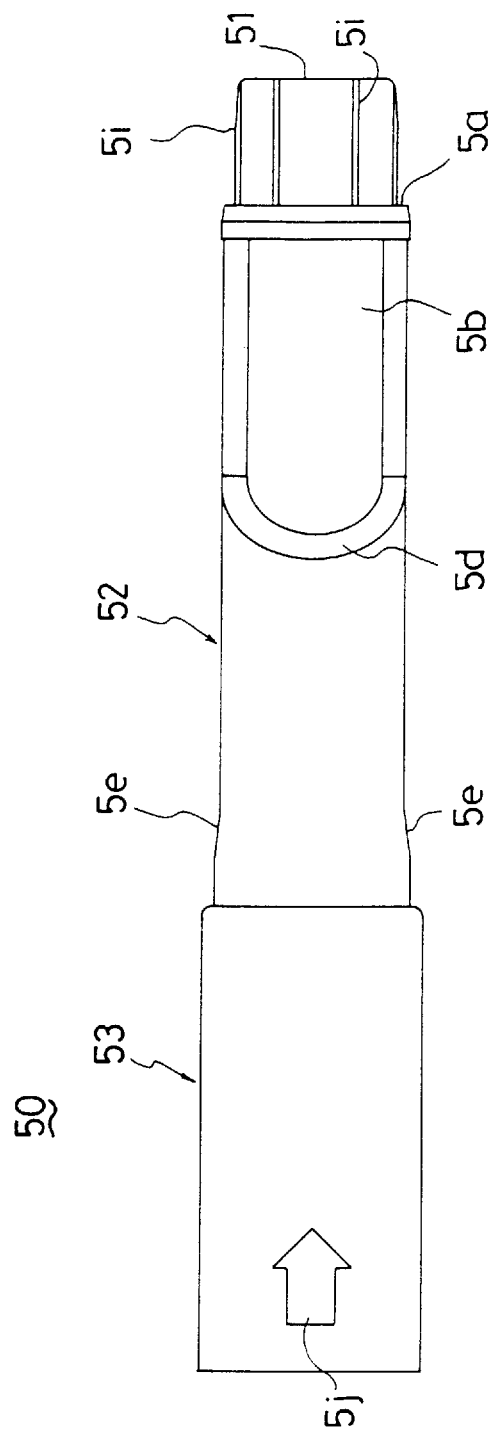
FIG. 28 is a front view showing a urine taking cap according to the embodiment 4.
Figure 29:
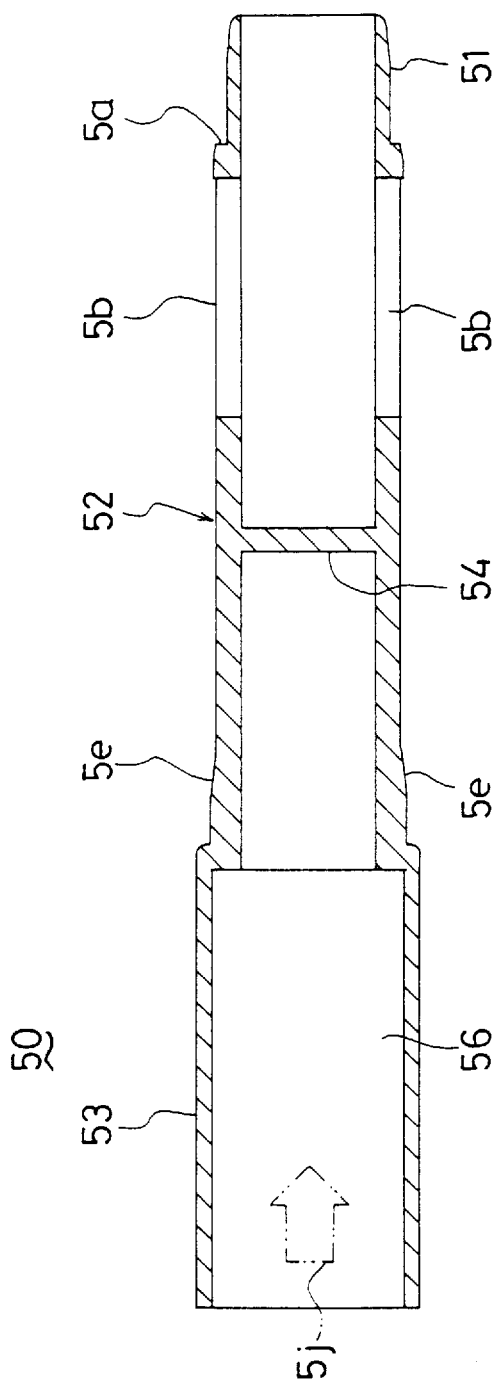
FIG. 29 is a longitudinally sectional view showing the urine taking cap according to the embodiment 4.

FIGS. 27 to 29 show an embodiment of the invention as defined in claim 12, in which the urine sampling vessel 10 of the embodiment 2 is changed into the slender urine sampling vessel 10 of the embodiment 1.

More specifically, while a vessel body 20 of the present embodiment has a small diameter in the same manner as the vessel body 20 of the embodiment 1, it is slightly tapered and a urine sampling inlet or the like is not formed thereon.

A cover cylinder 30 is formed like a taper corresponding to the vessel body 20, and has a blocking end formed like a semicircle.

A urine taking cap 50 is a cylinder in which a fitting cylinder section 51, a urine sampling cylinder section 52 and a grip section 53 are continuously formed in order in the same manner as in the embodiment 2, and has a small diameter in the same manner as in the embodiment 1.

The fitting cylinder section 51 has projection parts 5i, 5i, . . . formed thereon in the same manner as in the embodiment 3, while the urine sampling cylinder section 52 is long and one urine sampling inlet 5b is formed on an inner end side, that is, a fitting cylinder section 51 side.

Furthermore, the grip section 53 has a greater diameter than that of the urine sampling cylinder section 52, has a holding hole 56 of a cover cylinder 30 formed thereon in the same manner as in the embodiment 1, and has no extension cylinder 5g provided thereon unlike the embodiment 2. The holding hole 56 is opened on an outer end face of the grip section 53, and is formed such that an opened end of the cover cylinder 30 can be freely inserted therein and removed therefrom in the same manner as in the embodiment 1. In addition, an arrow 5j is formed by piercing the grip section 53 in the same manner as in the embodiment 3.

According to the present embodiment, consequently, the cover cylinder 30 is kept inserted in the holding hole 56 when taking urine, and the cover cylinder 30 is pulled out of the urine taking cap 50 and the vessel body 20 is inserted therein after taking the urine.

Other structures and functions are the same as in the embodiment 2.

According to the present embodiment described above, the cover cylinder 30 is held in the holding hole 56 of the urine taking cap 50. Consequently, the cover cylinder 30 can be prevented from being lost, and covering operation can be performed rapidly and easily after taking the urine.

One urine sampling inlet 5b is formed on the urine taking cap 50. Therefore, the urine taking cap 50 can be easily molded and become inexpensive.

Since the vessel body 20 can be easily inserted and removed by the projection parts 5i, 5i, . . . , it is easy to take the urine and perform a urinalysis.

Other effects are the same as in the embodiment 2.

-Other Variant-

While the knurling notch 44 has been formed on the cap body 41 in the embodiment 1, it is not necessary to always form the knurling notch in the present invention.

It is not necessary to always form the examination opening 22 of the embodiment 1 in the invention as defined in claim 1. In other words, the cap 40 may be always removed during the examination.

In the invention as defined in claims 1 to 5, it is not necessary to always form the flange section 45 of the embodiment 1 on the cap 40. The cap 40 has the outer shape of a cylinder.

The number of the urine sampling inlets 21, 21, . . . of the vessel body 20 is not restricted to eight as described in the embodiment 1, and the shape thereof is not restricted to the embodiment.

While the grip section 53 of the urine taking cap 50 can be made elastic by the extension cylinder 5g in the embodiment 2, the grip body 5f itself may be formed telescopically. In the invention as defined in claim 7, it is not necessary to always form the grip section 53 elastically.

In the embodiments 2 to 4, the shapes of the first urine sampling inlet 5b and the second urine sampling inlet 5c are not restricted thereto. In addition, the number of the second urine sampling inlets 5c in the embodiment 2 is not restricted to two.

While the grip section 53 has the shape of a cylinder in the embodiments 2 and 3, it may be rectangular or the like in the invention as defined in claims 7 to 11.

[Industrial Applicability]

As described above, the urine sampling vessel according to the present invention is very useful in taking urine when performing a urinalysis in hospitals and the like.

We claim:

1. A urine sampling vessel comprising:
   a slender cylindrical vessel body having an end blocked and the other end opened, and having a urine sampling inlet opened in a central portion thereof;
   a cover cylinder of a flexible material having a cylindrical body with an end blocked and the other end opened, formed such that the vessel body can be inserted into the cover cylinder with the cylindrical body of the cover cylinder in tight contact with the central portion of the vessel body so as to block the urine sampling inlet; and
   a cap having a blocking plug section formed thereon, the blocking plug section being freely removed from and attached to the opened end of the vessel body so as to open and close the opened end of the vessel body.

2. The urine sampling vessel as defined in claim 1, wherein the cap constitutes a means for mounting the vessel body in axial alignment with the cover cylinder with the open end of the cover cylinder facing the opened end of the vessel body, wherein said means for mounting comprises:
   the blocking plug section of the cap being protruded from an end of a cap body, and being formed like a short column so as to be detachably fitted in the opened end of the vessel body, and
   the cap body has a holding hole formed thereon, the holding hole being opened on the other end face of the cap body and enabling the end of the cover cylinder to be detachably fitted therein.

3. The urine sampling vessel as defined in claim 1, wherein a cap body has an engagement groove formed thereon, the engagement groove being connected to an outer periphery of a base end of the blocking plug section and causing the opened ends of the vessel body and the cover cylinder to be inserted therein with the vessel body inserted in the cover cylinder.

4. The urine sampling vessel as defined in claim 1, wherein the vessel body has a protrusion formed on an outer peripheral face thereof, to which the cover cylinder is attached by pressure when putting on the cover cylinder.

5. The urine sampling vessel as defined in claim 1, wherein a flange section extending outward is formed on an end on a blocking plug section side of a cap body.

6. A urine sampling vessel comprising:
   a slender cylindrical vessel body having an end blocked and the other end opened, and having a urine sampling inlet opened in a central portion thereof;
   a cover cylinder having a cylindrical body with an end blocked and the other end opened, formed such that the vessel body can be inserted in tight contact therewith and pulled out thereof, and put on the vessel body so as to block the urine sampling inlet; and
   a cap having a blocking plug section formed thereon, the blocking plug section being freely removed from and attached to the opened end of the vessel body so as to open and close the opened end of the vessel body;
   wherein the vessel body has an examination opening for a urinalysis formed from the urine sampling inlet toward an opened end side.

7. The urine sampling vessel as defined in claim 6, wherein the cap constitutes a means for mounting the vessel body in axial alignment with the cover cylinder with the open end of the cover cylinder facing the opened end of the vessel body, wherein said means for mounting comprises:
   the blocking plug section of the cap being protruded from an end of a cap body, and being formed like a short column so as to be detachably fitted in the opened end of the vessel body, and
   the cap body has a holding hole formed thereon, the holding hole being opened on the other end face of the cap body and enabling the end of the cover cylinder to be detachably fitted therein.

8. The urine sampling vessel as defined in claim 6, wherein the cover cylinder is formed of a flexible material.

9. The urine sampling vessel as defined in claim 6, wherein a cap body has an engagement groove being connected to an outer periphery of a base end of the blocking plug section and causing the opened ends of the vessel body and the cover cylinder to be inserted therein with the vessel body inserted in the cover cylinder.

10. The urine sampling vessel as defined in claim 6, wherein the vessel body has a protrusion formed on an outer peripheral face thereof, to which the cover cylinder is attached by pressure when putting on the cover cylinder.

11. The urine sampling vessel as defined in claim 6, wherein a flange section extending outward is formed on an end on a blocking plug section side of a cap body.

12. A urine sampling vessel comprising:

a cylindrical vessel body having an end blocked and the other end opened, and capable of housing taken urine;

a urine taking cap having a hollow fitting cylinder section formed like a cylinder which is detachable from the opened end of the vessel body and having both end faces opened, a urine sampling cylinder section formed like a cylinder which has an open inner end side connected to an outer end of the fitting cylinder section and has an outer end side blocked by a blocking wall and having a urine sampling inlet penetrating from an outer peripheral face to an inner peripheral face, and a grip section formed in connection to an outer end of the urine sampling cylinder section so as to be freely gripped, the blocking wall closing off the urine sampling cylinder section relative to said grip section; and a cover cylinder having an end blocked and the other end opened, and formed to enable the vessel body to be freely inserted therein and pulled out thereof, the opened end closing the urine sampling inlet of the urine taking cap and capable of being detachable from the outer peripheral face of the outer end of the urine sampling cylinder section in the state in which the vessel body having the urine taking cap attached to the fitting cylinder section is inserted within the cover cylinder.

13. The urine sampling vessel as defined in claim 12, wherein the outer peripheral face of the outer end of the urine sampling cylinder section in the urine taking cap is formed like a tapered face whose diameter is increased toward an outer end such that the opened end of the cover cylinder is fitted in tight contact therewith.

14. The urine sampling vessel as defined in claim 12, wherein a ring protrusion is formed on an outer peripheral face of a connecting portion of the urine sampling cylinder section and the grip section.

15. The urine sampling vessel as defined in claim 12, wherein the grip section of the urine taking cap has a grip body in which an extension cylinder having a bottom or no bottom is fitted so as to be freely slided.

16. The urine sampling vessel as defined in claim 12, wherein the urine sampling inlet of the urine taking cap is formed by cutting out a half of the urine sampling cylinder section in a circumferential direction.

17. The urine sampling vessel as defined in claim 12, wherein the grip section of the urine taking cap has a holding hole opened on an outer end face thereof and capable of causing the end of the cover cylinder to be freely inserted therein and removed therefrom.

* * * * *